(12) United States Patent
Mehta

(10) Patent No.: US 6,228,806 B1
(45) Date of Patent: *May 8, 2001

(54) BIOCHEMICAL FERTILIZER COMPOSITION

(75) Inventor: Raj J. Mehta, King of Prussia, PA (US)

(73) Assignee: Organica Inc., Norristown, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,058

(22) Filed: Oct. 6, 1998

Related U.S. Application Data

(63) Continuation-in-part of application No. 08/925,990, filed on Sep. 9, 1997, now abandoned.

(51) Int. Cl.[7] .................................................... A01N 63/00
(52) U.S. Cl. ............................................................. 504/117
(58) Field of Search ............................................... 504/117

(56) References Cited

U.S. PATENT DOCUMENTS 4,642,131 * 2/1987 Hoitlink ...................................... 71/6

OTHER PUBLICATIONS

The American Heritage Dictionary, 2nd Ed., Houghton Miffin Co. Boston, pp. 303, 498, 1976.*

* cited by examiner

Primary Examiner—Jose G. Dees
Assistant Examiner—Alton Pryor
(74) Attorney, Agent, or Firm—Henry E. Millson, Jr.

(57) ABSTRACT

Fertilizer compositions comprising:
 A) an effective quantity of an inorganic or organic fertilizer; and
 B) a quantity of beneficial microorganisms sufficient to further enhance plant growth when the fertilizer composition is applied to soil and/or control pathogens in the soil, and methods for their use.

20 Claims, No Drawings

BIOCHEMICAL FERTILIZER COMPOSITION

This application is a continuation-in-part of application Ser. No. 08/925,990, filed Sep. 9, 1997 now abandoned.

FIELD OF THE INVENTION

This invention relates to fertilizer compositions and methods for their use.

BACKGROUND OF THE INVENTION

The continuous use of chemical pesticides on plants, bushes and trees and especially those producing crops, has created an imbalance of the microbial eco-system in the soil under them. This results in the need for larger quantities of the chemical pesticides to maintain the same level of crop production, as well as an increased need for fertilizers.

One method used to try to overcome this problem is to use organic fertilizers, such as activated sludge, municipal compost, animal manures such as cow manure, and the like that provide beneficial microbes to improve crop productivity. However, a major drawback of many if not all of these organic fertilizers is the presence in them of toxic chemicals and/or toxic metals, that then accumulate in the soil.

DESCRIPTION OF THE INVENTION

Other than in the operating examples, or where otherwise indicated, all numbers expressing quantities of ingredients or reaction conditions used herein are to be understood as modified in all instances by the term "about".

It has now been discovered that a fertilizer composition that overcomes all of the above drawbacks to the use of pesticides and conventional inorganic and organic fertilizers is a fertilizer comprising:

A) an inorganic fertilizer and/or an organic fertilizer which is free or substantially free from toxic chemicals and toxic metals, and B) an effective quantity of beneficial microorganisms that a) enhance plant growth and, where applicable, crop production, and/or b) control various types of pathogens in the soil, optionally in combination with nutrients selected to maintain the viability of the microorganisms and/or increase their population. Such nutrients are well known to those skilled in microbiology.

The term "substantially free" used above means that the level of toxic chemicals and/or toxic metals in the organic fertilizer is so low that they are not detrimental to the soil or to plants growing in the soil to which the organic fertilizer is applied.

It is to be understood that use of the term "plant" in the specification and in the claims is meant to include both crop producing and non-crop producing plants, bushes, and trees.

Component A) of the present compostion can be a conventional balanced inorganic fertilizer e.g. having an N:P:K ratio of 6:10:4; 7:5:5; 9:13:7; 18:6:12; 19:8:10; 20:3:3; 25:4:4; 28:4:4; 32:10:10, and the like. These numbers show the percentage of total nitrogen, available phosphorous pentoxide ($P_2O_5$), and soluble potash ($K_2O$). This invention is of course not limited by the ratio of nitrogen to phosphorous to potassium in the inorganic fertilizer. The particular inorganic fertilizer selected will depend on the requirements of the soil to be fertilized.

Nitrogen can be present in the inorganic fertilizer in any convenient form, such anhydrous ammonia, aqueous ammonia, ammonium salts such as ammonium nitrate, calcium ammonium nitrate, ammonium phosphate, ammonium sulfate, and ammonium sulfate nitrate, sodium nitrate, potassium nitrate, urea, urea-formaldehyde reaction product, and the like.

Phosphorous can be present in any convenient water soluble form, such as $CaHPO_4$, $Ca(H_2PO_4)_2$, single superphosphate (made by reacting ground phosphate rock with 70% sulfuric acid), ammonium phosphate, nitrophosphates, monorthophosphates such as liquid ammonium polyphosphate, and the like.

Potassium can be present as commercial potash, potassium chloride, carnallite ($KCl. MgCl_2. 6H_2O$), potassium sulfate, potassium nitrate, and the like.

Dry blended urea, diammonium phosphate, and potash is a common balanced inorganic fertilizer. While urea and possibly other nitrogen sources may be considered to be organic compounds, fertilizers containing them are predominantly inorganic and are commonly referred to as inorganic fertilizers.

The predominantly inorganic fertilizers used in the practice of the invention can optionally contain up to 50% by weight and preferably up to 35% by weight of organic nitrogen-containing compounds as all or part of the nitrogen source.

In addition to the primary nutrients, i.e. nitrogen, phosphorous and potassium, secondary nutrients can be present as needed, such as calcium, magnesium, and sulfur. Also, micronutrient elements can also be added if desired such as boron, manganese, zinc, copper, iron, and molybdenum.

While balanced inorganic fertilizers are most commonly used, inorganic fertilizers deficient in one or more of nitrogen, phosphorous and potassium can be used in the practice of the invention, as soil conditions may dictate, e.g. having an N:P:K ratio of 6:2:0; 0:10:0 (bone meal); 16:20:0 (ammonium phosphate); and the like.

Organic fertilizers that are free or substantially free from toxic chemicals and/or metals that can be used as component A), either alone or in combination with an inorganic fertilizer, include processed animal body and vegetable products such as blood meal, cottonseed meal, ocean kelp meal, fish fertilizers such as fish emulsion, feather meal, and the like. Such organic fertilizers do not normally contain component B) microorganisms, at least not in any meaningful quantity.

Component B) can be any beneficial microbial organism or combination of organisms known to enhance the quality of soil for the growth of plants. Such micorganisms include those from the genera Bacillus, Clostridium, such as *Clostridium pasteurianum,* Rhodopseudomonas, such as *Rhodopseudomonas capsula,* and Rhizobium that fix atmospheric nitrogen; phosphorous stabilizing Bacillus organisms such as *Bacillus megaterium;* cytokinin producing microorganisms such as *Azotobacter vinelandii;* and microorganisms from the genera Pseudomonas, such as *Pseudomonas fluorescens,* Athrobacter, such as *Anthrobacter globii,* Flavobacterium such as Flavobacteriium sp., Saccharomyces, such as *Saccharomyces cerevisiae,* and the like.

Microorganisms useful in the practice of the invention can be selected from one or more of bacteria, fungi, and viruses that have utility in soil enhancement. Viruses such as the NPV viruses (nuclear polyhedrosis virus) such as the cabbage looper nuclear polyhedrosis virus are examples of useful viruses.

Microorganisms, (bacteria, fungi and viruses) that control various types of pathogens in the soil include microorganisms that control soil-born fungal pathogens, such as Trichoderma sp., *Bacillus subtilis,* Penicillium sp,; microorganisms that control insects, such as Bacillus sp. e.g. *Bacillus popalliae;* microorganisms that act as herbicides, e.g. Alternaria sp., and the like.

All of the above microorganisms are well known and are readily available from public depositories including ATCC and NRRL.

Optional components that can also be present in the fertilizer compositions of the invention include natural enzymes, growth hormones such as the gibberellins (gibberellic acid and gibberellin plant growth hormones), and control agents including Pesticides such as acaracides and molluskicides, insecticides, fungicides, nematocides, and the like, depending of course on their compatibility with the component B) microorganisms. Compounds useful as control agents may have one activity only, but frequently are effective in more than one of the above categories. Examples of control agents that can be used in the compositions of the invention, depending on component B) compatibility, include inorganic compounds such as elementary sulfur and inorganic sulfur compounds, e.g. calcium polysulfide and sodium thiosulfate, which are effective fungicides, copper, zinc, and other metal in organics such as copper carbonate copper oxychloride, copper sulfate, and copper zinc sulfate. Organometallic compounds such as iron and tin compounds, e.g. triphenyl tin hydroxide exhibit both insecticidal and pesticidal activity. Saturated higher alkyl alcohols, either straight or branched chain, such as nonyl and decyl alcohol, can be present as insecticides. Aldehydes such as metaldehyde is an effective molluskicide, e.g. useful against snails. Carbonic acid derivatives, especially their mixed esters, are potent acaracides and fungicides, and when sulfur is also present, e.g. mixed esters of thio- and di-thiocarbonic acids, activity is further increased. 6-methylquinoxaline-2,3-dithiocyclocarbonate is an effective acaricide, fungicide, and insecticide. Carbamic acid derivatives such as aryl esters of N-methylcarbamnic acid, e.g. 1-naphthyl-N-methylcarbamate can also be used. Halogen substituted aliphatic monobasic and dibasic carboxylic acids are effective pesticides. Natural pyrethrins and their synthetic analogs are also effective pesticides. Salicylanilide is effective against leaf mold and tomato brown spot. Hetercyclic compounds possessing insecticidal and/or fungicidal activity can also be used. Halogen derivatives of benzene, such as paradichlorobenzene, are effective pesticides, often used against the sugarbeet weevil. Chitin-containing products are effective menatocides. Other compounds that can be used include aliphatic mercaptans having four or fewer carbon atoms, organic sulfides and thioacetals, nitro compounds such as chloropicrin dichloronitroethane, and chloronitropropane, copper and zinc inorganic and organic compounds, e.g. copper linoleate, copper naphthenate, etc., organophosphorous compounds of which there are well over a hundred, e.g. DDVP, tris-(2,4-diphenoxyethyl) phosphite, derivatives of mono- and dithiophosphoric acids, such as 0,0-diethyl S [2-ethylthio)-ethyl]phosphorodithioate, phosphoric acid derivatives, pyrophosphoric acid derivatives and phosphonic acid derivatives, quinones, sulfonic acid derivatives, thiocyanates and isocyanates, phytoalexins, insect killing soaps such as potassium fatty acid salts, and antiallatotropins such as 7-methoxy-2,2-dimethylchromene and the 6,7-dimethoxy analog. Diatomaceous earth can be used, which kills crawling insects.

These optional components can comprise from 0.001 to 10% or more by weight of the fertilizer composition. Also, alkalizing agents such as ground limestone and acidifying agents such as inorganic acids or acid salts can be added as needed or desired.

The relative quantities of components A) and B) in the compositions of the invention are dependent in part on the activity of the microorganisms selected for component B). Preferably, component B) will consist of from $1 \times 10^5$ to 1,000 million microorganisms per gram of the fertilizer composition, and more preferably from 1 million to 100 million microorganisms per gram of fertilizer compostion, with or without added nutrients for the microorganisms.

The fertilizer compositions of the invention can be in solid form or in the form of an aqueous solution. Solid forms include powders and larger particulate forms, e.g. from 20 to 200 mesh.

Where the fertilizer compositions are in solid form and component B) microorganisms are sensitive to light, air, or compounds in fertilizer component A) or to optional added components, the microorganisms can be separately encapsulated in water soluble coatings, e.g., dyed or undyed gelatin spheres or capsules, or by micro-encapsulation to a free flowing powder using one or more of gelatin, polyvinyl alcohol, ethylcellulose, cellulose acetate phthalate, or styrene maleic anhydride. The separately encapsulated microorganisms can then be mixed with the powder or larger particulates of component A) (which is not encapsulated) and any optional components. Encapsulation of the microorganisms preferably includes nutrients as well as the microorganisms.

The presence of the component B) microorganisms in the fertilizer compositions of the invention provides further enhancement of plant growth, and where applicable, crop production, i.e. by further enhancement is meant benefits in plant growth and crop production in addition to the benefits provided by the fertilizer component A), and/or provides control of pathogens in the soil. The fertilizer compositions of the invention can be added to soil to replenish chemical elements that have been reduced or exhausted by the soils from crops previously grown, or which have been leached from the soils as a result of poor tillage practices, overirrigation, or natural flooding, and to add nutrients to soils naturally deficient in them. The selection of the component A) inorganic fertilizer can be customized to the nutrient content of the soil to obtain particular growing objectives.

The present invention also relates to a method for enchancing the ability of soil to grow plants comprising the steps of:

I) analyzing the soil to determine (a) its nutrional requirements and (b) the presence of pathogens harmful to plants to be grown in the soil;

II) formulating a fertilizer composition to satisfy the nutrional requirements of the soil, to provide beneficial microorganisms to further enhance plant growth, and where needed to provide beneficial microorganisms and/or chemical pest control agents to control pathogens found to be present; and III) applying the formulated fertilizer composition to the soil.

The invention also relates to a method for formulating a fertilizer composition comprising the steps of:

I) analyzing the soil to determine (a) its nutrional requirements, and (b) the presence of pathogens harmful to plants to be grown in the soil; and II) formulating a fertilizer composition to satisfy the nutrional requirements of the soil, to provide beneficial microorganisms to further enchance plant growth, and where needed to provide beneficial microorganisms and/or chemical pest control agents to control pathogens found to be present.

In the above methods, the fertilizer composition formulated in step II can be, and preferably is, a fertilizer composition of the invention described above.

The invention will be illustrated but not limited by the following examples.

EXAMPLES

Example 1

A fertilizer composition containing urea, ammonium phosphate, and potassium5 chloride in a ratio of N:P:K of 25:4:4 with a particle size of 100 mesh is intimately mixed with 1 million–500 million *clostridium pasteurianum,* per gram of the composition and 1 million–500 million *Rhodopseudomonas capsula* per gram of the composition to form the finished fertilizer composition.

Example 2

A fertilizer composition containing ammonium sulfate, triple superphosphate, and carnallite in a ratio of 32:10:10 with a particle size of 50 mesh is intimately mixed with 1 million–100 million *Bacillus megaterium* or *Bacillus subtilis* in the form of gelatin microcapsules of about 1000 micron diameter, per gram of the composition, to form the finished fertilizer composition.

Example 3

A liquid fertilizer composition is formulated containing $KNO_3$, $Ca(H_2PO_4)_2$, and KCl in a ratio of N:P:K: of 18:6:12 in water in a concentration of 10% solids. To this aqueous solution is added 1 million–100 million *Athrobacter globii* per gram of solids.

What is claimed is:

1. A biochemical fertilizer composition comprising:
    A) a fertilizing effective quantity of a fertilizer for fertilizing soil which is either a) an essentially inorganic fertilizer, b) an organic fertilizer selected from the group consisting of blood meal, cottonseed meal, ocean kelp meal, and fish fertilizer, or c) a mixture of components a) and b); and
    B) a quantity of beneficial microorganisms in an amount of a least about $1 \times 10^5$ microorganisms per gram of fertilzer sufficient to (a) further enhance plant growth when the fertilizer composition is applied to the soil; and/or b) control one or more pathogens in the soil; wherein component B) but not component A) is optionally encapsulated in a water-soluble coating and wherein component A) a) can contain up to about 50% by weight of organic nitrogen-containing compounds.

2. The fertilizer composition of claim 1 wherein the quantity of component B) is also sufficient to further improve crop production in crop producing plants.

3. The fertilizer composition of claim 1 wherein component A)a) is present and is a balanced fertilizer containing fertilizing effective quantities of nitrogen, phosphorous, and potassium.

4. The fertilizer composition of claim 1 wherein component B) comprises from about $1 \times 10^5$ to about 1,000 million microorganisms per gram of fertilizer composition.

5. The fertilizer composition of claim 1 wherein the composition also contains at least one additional plant nutrient.

6. The fertilizer composition of claim 1 wherein the composition also contains at least one of a gibberellin, an acaracide, an insecticide, a fungicide, a nematocide, and a molluskicide.

7. The fertilizer composition of claim 3 wherein nitrogen is in the form of at least one compound selected from the group consisting of ammonia, an ammonium salt, sodium or potassium nitrate, urea, and urea-formaldehyde reaction product.

8. The fertilizer composition of claim 3 wherein phosphorous is in the form of at least one compound selected from the group consisting of $CaHPO_4$, $Ca(H_2PO_4)_2$, single superphosphate, triple superphosphate, ammonium phosphate, a nitrophosphate and a monorthophosphate.

9. The fertilizer composition of claim 3 wherein potassium is in the form of at least one compound selected from the group consisting of potash, potassium chloride, carnallite, potassium sulfate, and potassium nitrate.

10. The fertilizer composition of claim 1 wherein component B) is at least one microorganism selected from genera Bacillus, Clostridium, Rhodopseudomonas, Pseudomonas, Arthrobacter, Flavobacteria, Saccharomyces, Azotobacter, Trichoderma, Pencillium, and Alternaria.

11. The fertilizer composition of claim 1 wherein the composition is in a powder or larger particulate form.

12. The fertilizer composition of claim 11 wherein component B) is in the form of particles encapsulated in a water-soluble coating.

13. The fertilizer composition of claim 12 wherein component B) is in the form of microcapsules.

14. The fertilizer composition of claim 12 wherein component B) also contains nutrients for the microorganisms.

15. A method of enhancing plant growth and/or crop production comprising applying to the soil in which plants are growing or are to be grown a growth enhancing quantity of the fertilizer composition of claim 1; wherein component A) thereof is formulated to fulfill the requirements of the plants and the soil to which the composition is applied, and component B) is formulated to enhance the growth of the plants and/or control one or more pathogens.

16. The composition of claim 1 wherein component A) can optionally contain up to about 35% by weight of organic nitrogen-containing compounds.

17. A method for formulating a fertilizer composition comprising the steps of:
    I) analyzing the soil to determine (a) its nutritional requirements and (b) the presence of pathogens harmful to plants to be grown in the soil; and
    II) formulating a fertilizer composition to satisfy the nutritional requirements of the soil, to provide beneficial microorganisms to further enhance plant growth, and where needed to provide beneficial microorganisms and/or chemical pest control agents to control pathogens found to be present by mixing together, either in dry form or in water, the predetermined quantities of the fertilizer components comprising the biochemical fertilizer composition of claim 1.

18. A method for enhancing the ability of soil to grow plants comprising the steps of:
    I) analyzing the soil to determine its nutrional requirements, and the presence of pathogens harmful to plants to be grown in the soil;
    II) formulating a fertilizer composition in accordance with claim 1 to satisfy the nutrional requirements of the soil, to provide beneficial microorganisms to further enchance plant growth, and where needed to provide beneficial microorganisms and/or chemical pest control agents to control pathogens found to be present; and III) applying the formulated fertilizer composition to the soil.

19. The method of claim 15 wherein the quantity of component B) is also sufficient to further improve crop production in crop producing plants.

20. The method of claim 18 wherein the quantity of component B) is also sufficient to further improve crop production in crop producing plants.

* * * * *